US005554576A

United States Patent [19]
Mookerjee et al.

[11] Patent Number: 5,554,576
[45] Date of Patent: Sep. 10, 1996

[54] METHOD AND COMPOSITION FOR ENHANCING UPTAKE AND TRANSPORT OF BIOACTIVE AGENTS IN PLANTS

[75] Inventors: Pradip K. Mookerjee, Flemington, N.J.; Ahmad Omid, Walnut Creek, Calif.

[73] Assignee: Tomen Corporation, Tokyo, Japan

[21] Appl. No.: 490,093

[22] Filed: Jun. 6, 1995

Related U.S. Application Data

[63] Continuation of Ser. No. 39,171, filed as PCT/US90/05973, Oct. 17, 1990, published as WO92/06596 abandoned.

[51] Int. Cl.⁶ .......................... A01N 25/30; C11D 1/14; C11D 1/34; C11D 1/04
[52] U.S. Cl. .......................... 504/116; 504/348; 424/405; 252/351; 71/DIG. 1
[58] Field of Search .................... 504/116, 348; 424/405; 252/351, 107, 108, 109, 121, 132, 135, 550, 554, 555, 556, 558, 174.16, 174.21, 174.22; 514/937–943, 975; 71/DIG. 1

[56] References Cited

U.S. PATENT DOCUMENTS

| | | | |
|---|---|---|---|
| 3,950,420 | 4/1976 | Sawaki et al. | 71/88 |
| 4,642,338 | 2/1987 | Rogers et al. | 534/558 |
| 4,666,510 | 5/1987 | Watson et al. | 71/103 |
| 4,834,908 | 5/1989 | Hazen et al. | 252/356 |

*Primary Examiner*—S. Mark Clardy
*Attorney, Agent, or Firm*—Fish & Richardson P.C.

[57] ABSTRACT

Methods and compositions are provided for enhancing uptake of a plant active agent, particularly herbicides, which have structures capable of equilibrating to acidic and basic species in the presence of water. The bioactive agent is mixed with an uptake and transport-enhancing adjuvant comprising an anionic surfactant and a mixture of water-immiscible, low-vapor pressure, vegetable-derived oils.

58 Claims, No Drawings

METHOD AND COMPOSITION FOR ENHANCING UPTAKE AND TRANSPORT OF BIOACTIVE AGENTS IN PLANTS

This is a continuation of application Ser. No. 08/039,171, filed Jun. 17, 1993, now abandoned which was filed under 35 USC 371 as a continuation of PCT/US90/05973, filed 17 Oct. 1990.

The present invention is directed to a method and composition for enhancing uptake and transport of bioactive agents, such as herbicides, insecticides, fungicides, plant growth regulators, fertilizers, and the like, in plants.

BACKGROUND OF THE INVENTION

Many bioactive chemicals, and in particular herbicides, have been developed which are either highly selective to particular plant species, climate sensitive or are in some instances very expensive to use. Also, it is recognized that only a portion of an applied bioactive agent, such as a herbicide, is actually biologically engaged in the plant. Thus more efficient utilization of the-applied bioactive agent is required. It has been surprisingly found that uptake and transport of plant active agents, particularly herbicides, where the bioactive agent has a molecular structure capable of equilibrating in presence of water to acidic and basic species, can be enhanced by use in conjunction with an adjuvant comprising anionic surfactants and low-vapor-pressure, water-immiscible liquids.

It is an object of the present invention, therefore, to provide a plant active composition comprising a bioactive agent and adjuvant which provides more effective use of the bioactive agent by enhancing uptake and transport into the plant.

Another object of the present invention is to increase the efficacy of herbicides and other plant-active agents.

These and other objects will be apparent from the following description, disclosure and by practice of the invention.

SUMMARY OF THE INVENTION

A method and composition are provided for enhancing uptake of bioactive agents in plants whereby a composition is applied to the plant having the following components: a bioactive agent having a molecular structure capable of equilibrating to acidic and basic species in water and an uptake-enhancing adjuvant. The adjuvant comprises 20–60% (w/w) of an anionic surfactant; 40–60% (w/w) of fatty acids, fatty acid esters or mixtures thereof; and 10–40% (w/w) of polyalkylene glycol esters of fatty acids. A preferred class of anionic surfactants comprises phosphate esters of the formula

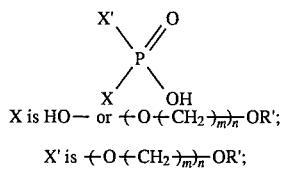

X is HO— or $+O+CH_2)_m)_n-OR'$;

X' is $+O+CH_2)_m)_n-OR'$;

wherein R' is an alkyl or alkaryl group containing 5–50 carbon atoms; m is 2 or 3; and n is an integer from 1 to about 50. The most preferred class of anionic surfactants are those in which m=2, n is from 2 to 9; R' is $C_{11}$–$C_{14}$ (if R' is alkyl) or R' is $C_{15}$–$C_{30}$ (if R' is alkaryl ). If R' is alkaryl, non-ylphenyl and dinonylphenyl groups are preferred.

Another class of anionic surfactants comprises those of the formula $R^5$—$SO_3H$ wherein $R^5$ is linear or branched alkyl or alkenyl containing 6 to about 50 carbon atoms, or $R^5$ is

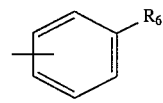

wherein $R^6$ is alkyl or alkenyl containing 1 to about 30 carbon atoms.

The adjuvant also comprises about 40–60% (w/w) of fatty acids, fatty acid esters or mixtures thereof. Lower alkyl esters are preferred.

The adjuvant also comprises 10–40% (w/w) of polyalkyleneglycol esters of fatty acids. Polyethylene glycol esters are particularly preferred, most preferably where the polyethylene glycol moiety has an average molecular weight in the range of about 200 to 1000.

Optionally, the adjuvant may contain 10–40% (w/w) of other components which are well known in the art as quality enhancement agents. These include antioxidants, emulsifiers, film formers and diluents.

DISCLOSURE OF THE PREFERRED EMBODIMENTS

The bioactive agent used in conjunction with the present invention may be any bioactive agent such as a herbicide, insecticide, fungicide, plant growth regulator, fertilizer, and the like, which has a molecular structure capable of equilibrating in an aqueous system to acidic and basic equilibrium species. These acidic and basic species are interconvertible by addition or removal of protons. For example, in the following generic representation of the equilibrium process, HA and A⁻ are in the acidic and basic forms of the bioactive agent:

$$HA \rightleftharpoons A^- + H^+$$

Particularly preferred bioactive agents are herbicides which are disclosed in Patent No. 4,440,566.

The adjuvant according to the present invention will comprise an anionic surfactant (which is acidic in water), and other low-vapor-pressure (less than 3 mm/Hg at 20° C), water immiscible-liquids, selected from the group which includes fatty acids, fatty-acid esters, and mixtures thereof, as described below.

Preferably all of these components will have a vapor pressure of less than 1 mm (at atmospheric pressure). It is a particular advantage of the adjuvant that the components have low volatility, which minimizes environmental pollution. Furthermore, the vegetable derived materials which are used (fatty acids and esters) are non-toxic and degrade rapidly in the environment. These are significant advantages over many adjuvants of the current art which contain hydrocarbons.

A preferred class of bioactive agents are herbicides of the structure

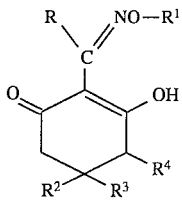

wherein
R is alkyl of 1 to 6 carbon atoms or phenyl; $R^1$ is haloalkenyl of 2 to 6 carbon atoms and 1 to 3 halogen atoms, p-halobenzyl or p-trifluoromethylbenzyl;

$R^2$ and $R^3$ are independently hydrogen, alkyl of 1 to 3 carbon atoms, alkylthio of 1 to 6 carbon atoms, or alkylthioalkyl of 2 to 8 carbon atoms;

$R^4$ is hydrogen or carbalkoxy of 2 to 4 carbon atoms.

Particularly, the preferred compounds are those wherein $R^4$ is hydrogen, and R is alkyl of 1 to 6 carbon atoms, and $R^1$ is haloalkenyl. Other preferred compounds are those wherein R is ethyl or propyl, and one of $R^2$ or $R^3$ is hydrogen and the other is alkylthioalkyl. Many of the preferred compounds are those in which R is ethyl or propyl and one of $R^2$ or $R^3$ is hydrogen and the other is 2-ethylthiopropyl and $R^1$ is haloalkenyl. The group $R^1$ may also be 3-trans-chloroallyl.

The anionic surfactants will be those with an acid dissociation constant (pKa) in the range of about 0.1 to 5.0, preferably from 1 to 5. A preferred class of anionic surfactants are alkoxylated phosphoric acid esters of the following formula

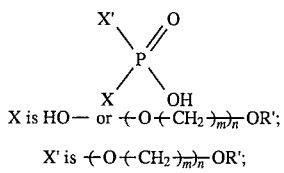

X is HO— or $-(O-(CH_2)_{\overline{m}})_{\overline{n}}OR'$;

X' is $-(O-(CH_2)_{\overline{m}})_{\overline{n}}OR'$;

wherein R' is an alkyl group or alkaryl group containing 5–50 carbon atoms m is 2 or 3; and n is an integer from 1 to 50.

Alkyl and alkaryl groups include, but are not limited to, decyl, lauryl, tridecyl, oleyl, stearyl, nonylphenyl, octylphenyl, dinonylphenyl, dioctylphenyl, didecylphenyl, octylnaphthyl, dioctylnaphthyl, and the like.

Preferably m=2, n is from 2 to 9 and R' is $C_{11}$–$C_{14}$ alkyl or $C_{15}$–$C_{30}$ alkaryl. The lauryl, tridecyl, nonylphenyl, and dinonylphenyl groups are preferred.

Another class of surfactants includes sulfonic acids of formulas $R^5$—$SO_3H$ wherein $R^5$ is linear or branched $C_6$ to $C_{50}$, alkyl or alkenyl or $R^5$ is

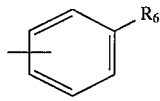

and $R^6$ is $C_1$–$C_{30}$ alkyl, preferably linear $C_8$–$C_9$. $R^5$ is preferably $C_{12}$–$C_{30}$ alkyl or alkenyl.

Particularly preferred anionic surfactants for use in the adjuvant are those in which X is OH or $-(O-(CH_2)_{\overline{m}})_{\overline{n}}OR'$. Particularly preferred anionic surfactants are those in which m is 2, n is 2 to 9, and most preferred R' is decyl, lauryl, tridecyl, or dialkylphenyl. The most preferred anionic surfactants are those in which R' is tridecyl or dinonylphenyl.

The low vapor-pressure, water-immiscible liquids which are particularly preferred are fatty acids and their ester derivatives. The adjuvant will comprise 40–60% (w/w) fatty acids or fatty acid esters, such as isostearic acid, methyl oleate and the like. Also, the adjuvant will contain from 10–40% (w/w) of a polyalkylene glycol ester of fatty acids. The polyalkylene glycol moiety which is particularly preferred in polyethylene glycol, typically having an average molecular weight in the range of 200 to 1000, with 400 being most preferred.

In a most particularly preferred composition, a cyclohexane dione herbicide concentrate (2 lb./gallon containing an emulsifier and a solvent) is used by combining a sufficient amount of such a concentrate to provide 0.1 lbs. (active basis) of the herbicide, with 20 gallons of water. A second composition, an adjuvant mixture, is made comprising 70% of fatty acid esters and 30 % of the mixture comprising a phosphoric ester surfactant wherein X=OH, m=2, n=3 and R'=tridecyl. The adjuvant mixture and the water mixture containing the herbicide are then mixed wherein the adjuvant weight to aqueous herbicidal mixture weight ratio is between about 1:5 and 1:1000, respectively. A particularly preferred ratio is between 1:200 and 1:300.

It is particularly advantageous in that while the cyclohexane dione herbicides, particularly those useful against grassy weeds, are normally applied at a rate of from 30 to 567 g/ha, according to the present invention they are equally efficacious when applied at about 40% or less of that rate with the uptake-enhancing agent.

Suitable bioactive agents which may be utilized in connection with the present invention include, but not limited to, compounds such as Herbicides
clethodim (SELECT)
4-chloro-2-oxo-3(2H) -benzothiazoleacetic acid (benazolin)
3-(1-methylethyl)-1(H)-2,1,3-benzothiadiazin-4(3H)-one 2,2-dioxide (bentazone, BASAGRAN)
3,5-dibromo-4-hydroxybenzonitrile (bromoxynil)
3-amino-2,5-dichlorobenzoic acid (chloramben, AMIBEN)
3,6-dichloro-2-pyridinecarboxylic acid (clopyralid, LONTREL)
2-[1-(ethoxyimino)butyl]-3-hydroxy-5-(tetrahydro-2H-thiopyran-3-yl)-2-cyclohexene-1 -one (cycloxydim)
(2,4-dichlorophenoxy)acetic acid (2,4-D)
3,6-dichloro-2-methoxybenzoic acid (dicamba, BANVEL)
N-(phosphonomethyl)glycine (glyphosate)
2-[4,5-dihydro-4-methyl-4-(1-methyethyl)-5-oxo-1H-imidazol-2-yl]-3-quinolinecarboxylic acid (imazaquin, SCEPTER)
4-amino-3,5,6-trichloro-2-pyridinecarboxylicacid (picloram, TORDON)
2-[1-(ethoxyimino)butyl]-5-[2-(ethylthio)propyl]-3-hydroxy-2-cyclohexen-1-one (sethoxydim, POAST)
5-[2-chloro-4-(trifluoromethyl)phenoxy]-2-nitrobenzoic acid (acifluorfen, BLAZER)

Fungicides
2,2'-methylenehis (4-chlorophenol) (dichlorophen)
5-butyl-2-(dimethylamino)-6-methyl-4 (1H)-pyrimidinone (dimethirimol)

Insecticides
O,S-dimethyl acetylphosphoramidothioate (ORTHENE)
cyano (3-phenoxyphenyl)methyl 14-chloro(1-methylethyl) benzene acetate (fenvalerate, PYDRIN)

PGR
2-(3-chlorophenoxy)propanoic acid (3-CPA, FRUITONE CPA)

(2-chloroethyl)phosphonic acid (ethephon)
1H-indole-3-acetic acid
1-naphthaleneacetic The compositions according to the present invention are beneficially employed to promote uptake and transport of systemic herbicides, fungitides, pesticides, plant growth regulators, fertilizers and the like. It is to be understood that combinations of the above bioactive agents can be employed, as in available commercial formulations, and are generally applied at rates recommended by the supplier of the bioactive agent. However, increased benefits with herbicides or other bioactive agents having the requisite proton exchange ability can be realized when the bioactive enhancing agent is utilized therewith.

A particularly preferred utilization is that with a herbicide as disclosed in U.S. Pat. No. 4,440,566 which is incorporated by reference herein in its entirety. As such, the herbicides may be used primarily as a post-emergent herbicide. The amount of active herbicidal compound administered will vary with the particular plant or plant growth medium which is to be contacted, the general location of an application, i.e., sheltered areas such as greenhouses, as compacted to exposed areas such as fields, as well as desired type of control. Generally, for illustrative purposes, under greenhouse conditions, for post-emergent herbicidal control, SELECT, a herbicidal compound having a cyclohexane dione moiety would normally be applied at a rate of about 28 g/ha. However, when used in conjunction with the bioactive enhancing agent the equivalent activity may be obtained within an application rate at 5 g/ha or less, with no damage to broadleaf crops (see Tables 1 through 5). Similar relative enhancement under field conditions is obtained (see Table 6). Normal field application rates of SELECT are about 30–120 g/ha (for control of annual grasses, and usually about 120–567 g/ha for control of established perennial species. Addition of 0.1–1% (v/v) (preferably 0.3–0.5% (v/v)) of the bioactive-enhancing agent to the aqueous spray solution of the herbicide enhances the activity and reduces the necessary rate of application of the herbicide.

The adjuvant may contain optional emulsifiers, dispersants, binders, stabilizers and the like, which are well known in the art as functional additives that optimize formulations.

Post-Emergent Herbicidal Test

The bio-active agent and adjuvant were homogeneously dispersed in water and sprayed on the plants. The compositions of the spray mixtures are indicated in the Tables 1–6. Each formulation was uniformly sprayed on plants. Greenhouse plants were 2 to 4" tall (approximately 5 to 25 plants per pot) at treatment. After the plants were sprayed and allowed to dry, they were placed in a greenhouse and then watered intermittently at their basess, as needed. The plants were observed periodically for phytotoxic effects and physiological and morphological responses to the treatment. After 3 weeks, the herbicidal effectiveness of the compound was rated based on these observations. A 0-to-100 scale was used, 0 representing no phytotoxicity and 100 representing complete kill. The application rates of Select were as % active ingredient. The results of these tests appear in the Tables 1–5.

The following examples are provided to assist in the understanding of the invention and are not to be construed as limiting the scope of the invention. In the following attached Tables 1–6 the herbicidally active compound (a herbicide disclosed in Pat. No. 4,440,566) known as Clethodim is used. It is usually sold as a formulation known as Select.

TABLE 1

Percent Phytotoxicity of Select With and Without Adjuvant on Grass and Broadleaf Plants
Greenhouse Test

| Weeds and Crop Plants | Select* 0 gr/ha Adjuvant 0.25% v/v | Select 28 gr/ha Adjuvant 0% v/v | Select 11 gr/ha Adjuvant 0.25% v/v | Select 11 gr/ha Adjuvant 0.125% v/v |
|---|---|---|---|---|
| Blackgrass | 0 | 91 | 90 | 88 |
| Wild Oats | 0 | 56 | 81 | 68 |
| Cheatgrass | 0 | 46 | 85 | 63 |
| Crabgrass | 0 | 43 | 76 | 71 |
| Barnyard Grass | 0 | 91 | 86 | 80 |
| Goosegrass | 0 | 90 | 90 | 80 |
| Sprangletop | 0 | 94 | 91 | 93 |
| Italian Ryegrass | 0 | 81 | 90 | 88 |
| Fall panicum | 0 | 91 | 91 | 91 |
| Proso millet | 0 | 88 | 90 | 90 |
| Yellow foxtail | 0 | 86 | 85 | 85 |
| Johnsongrass | 0 | 71 | 86 | 85 |
| Rice | 0 | 50 | 56 | 50 |
| Sorghum | 0 | 81 | 76 | 73 |
| Wheat | 0 | 40 | 46 | 26 |
| Field corn | 0 | 63 | 63 | 63 |
| MEAN GRASSES | 0 | 73 | 80 | 75 |
| Sugarbeets | 0 | 0 | 0 | 0 |
| Canola | 1 | 1 | 3 | 1 |
| Soybean | 1 | 1 | 1 | 3 |
| Cotton | 6 | 3 | 0 | 0 |
| MEAN BROADLEAF CR | 2 | 1 | 1 | 1 |

*Application rates of SELECT are given as active ingredient. The Adjuvant is 30% (wt.) alkylphosphoric acid ester (R' = tridecyl, m = 2, n = 3) 20% (wt.) PEG 400 dioleate, and 50% (wt.) methyl oleate (EMEREST 2301). The compositions are spray emulsions of the formulated active ingredient, adjuvant and water. Addition of adjuvant significantly improved the activity of Select.

TABLE 2

Percent Phytotoxicity of Select With and Without Adjuvant on Grass and Broadleaf Plants
Greenhouse Test

| Weeds and Crop Plants | Select* 0 gr/ha Adjuvant 0.25% v/v | Select 11 gr/ha Adjuvant 0% v/v | Select 11 gr/ha Adjuvant 0.25% v/v | Select 11 gr/ha Adjuvant 0.125% v/v |
|---|---|---|---|---|
| Blackgrass | 0 | 43 | 90 | 88 |
| Wild Oats | 0 | 0 | 81 | 68 |
| Cheatgrass | 0 | 0 | 85 | 63 |
| Crabgrass | 0 | 10 | 76 | 71 |
| Barnyard Grass | 0 | 50 | 86 | 80 |
| Goosegrass | 0 | 10 | 90 | 80 |
| Sprangletop | 0 | 3 | 91 | 93 |
| Italian Ryegrass | 0 | 0 | 90 | 88 |
| Fall panicum | 0 | 68 | 91 | 91 |
| Proso millet | 0 | 43 | 90 | 90 |
| Yellow foxtail | 0 | 28 | 85 | 85 |
| Johnsongrass | 0 | 15 | 86 | 85 |
| Rice | 0 | 0 | 56 | 50 |
| Sorghum | 0 | 46 | 76 | 73 |
| Wheat | 0 | 0 | 46 | 26 |
| Field corn | 0 | 13 | 63 | 63 |
| MEAN | 0 | 21 | 80 | 75 |

TABLE 2-continued

Percent Phytotoxicity of Select With and Without
Adjuvant on Grass and Broadleaf Plants
Greenhouse Test

| Weeds and Crop Plants | Select* 0 gr/ha Adjuvant 0.25% v/v | Select 11 gr/ha Adjuvant 0% v/v | Select 11 gr/ha Adjuvant 0.25% v/v | Select 11 gr/ha Adjuvant 0.125% v/v |
|---|---|---|---|---|
| GRASSES | | | | |
| Sugarbeets | 0 | 0 | 0 | 0 |
| Canola | 1 | 0 | 3 | 1 |
| Soybean | 1 | 3 | 1 | 3 |
| Cotton | 6 | 0 | 0 | 0 |
| MEAN BROADLEAF CR | 2 | 1 | 1 | 1 |

Conclusion:
Select at 11 gr/ha without the adjuvant has poor activity on grasses. The activity of Select is increased significantly by adding 0.125 or 0.25% (v/v.) adjuvant to the spray solution.

TABLE 3

Effect of Different Additives on the
Percent Phytotoxicity of Select
Greenhouse Test

| Weeds and Crop Plants | SELECT 0 gr/ha ADJUVANT 1% v/v | SELECT 5 gr/ha ADJUVANT 0% v/v | SELECT 5 gr/ha ADJUVANT 0.3% v/v | SELECT 5 gr/ha AGRIDEX ** 0.3% v/v | SELECT 0 gr/ha AGRIDEX 1% v/v |
|---|---|---|---|---|---|
| Blackgrass | 0 | 10 | 55 | 20 | 0 |
| Crabgrass | 0 | 10 | 90 | 30 | 0 |
| Goosegrass | 0 | 25 | 65 | 45 | 0 |
| Sprangletop | 0 | 10 | 90 | 30 | 0 |
| Italian Ryegrass | 0 | 30 | 90 | 75 | 0 |
| Proso millet | 0 | 80 | 94 | 90 | 0 |
| Wheat | 0 | 0 | 40 | 15 | 0 |
| Barley | 0 | 0 | 60 | 0 | 0 |
| MEAN GRASSES | 0 | 21 | 73 | 38 | 0 |

**Agridex is a commercial adjuvant containing 80% (wt) paraffinic oil and approximately 20% (wt) nonionic surfactant.

Conclusions:

1. Adjuvant is not phytotoxic even at 1%.

2. Adjuvant at 0.3% v/v in the spray solution is more effective than Agridex and dramatically enhances the activity of Select.

TABLE 4

Effect of Different Additives on the
Percent Phytotoxicity of Select
Greenhouse Test

| Weeds and Crop Plants | SELECT 0 gr/ha ADJUVANT 1% v/v | SELECT 5 gr/ha ADJUVANT 0% v/v | SELECT 5 gr/ha ADJUVANT 1% v/v | SELECT 5 gr/ha AGRIDEX 1% v/v | SELECT 0 gr/ha AGRIDEX 1% v/v |
|---|---|---|---|---|---|
| Blackgrass | 0 | 10 | 80 | 70 | 0 |
| Crabgrass | 0 | 10 | 90 | 70 | 0 |
| Goosegrass | 0 | 25 | 70 | 55 | 0 |
| Sprangletop | 0 | 10 | 90 | 40 | 0 |
| Italian | 0 | 30 | 90 | 75 | 0 |

TABLE 4-continued

Effect of Different Additives on the
Percent Phytotoxicity of Select
Greenhouse Test

| Weeds and Crop Plants | SELECT 0 gr/ha ADJUVANT 1% v/v | SELECT 5 gr/ha ADJUVANT 0% v/v | SELECT 5 gr/ha ADJUVANT 1% v/v | SELECT 5 gr/ha AGRIDEX 1% v/v | SELECT 0 gr/ha AGRIDEX 1% v/v |
|---|---|---|---|---|---|
| Ryegrass | | | | | |
| Proso millet | 0 | 80 | 95 | 80 | 0 |
| Wheat | 0 | 0 | 50 | 15 | 0 |
| Barley | 0 | 0 | 60 | 0 | 0 |
| MEAN GRASSES | 0 | 21 | 78 | 51 | 0 |

Conclusions:

5 gr/ha Select and 1% adjuvant resulted in 80% or higher control of five out of eight grassy species. The same rate of Agridex plus SELECT gave 80% control of one out of eight grassy species.

TABLE 5

Effect of Different Additives on the
Percent Phytotoxicity of Select
Greenhouse Test

| Weeds and Crop Plants | SELECT 0 gr/ha ADJUVANT 1% v/v | SELECT 11 gr/ha ADJUVANT 0% v/v | SELECT 11 gr/ha ADJUVANT 0.3% v/v | SELECT 11 gr/ha AGRIDEX 0.3% v/v | SELECT 0 gr/ha AGRIDEX 1% v/v |
|---|---|---|---|---|---|
| Blackgrass | 0 | 60 | 80 | 70 | 0 |
| Crabgrass | 0 | 65 | 95 | 80 | 0 |
| Goosegrass | 0 | 65 | 90 | 92 | 0 |
| Sprangletop | 0 | 57 | 98 | 50 | 0 |
| Italian Ryegrass | 0 | 70 | 95 | 98 | 0 |
| Proso millet | 0 | 90 | 100 | 95 | 0 |
| Wheat | 0 | 25 | 75 | 40 | 0 |
| Barley | 0 | 0 | 85 | 0 | 0 |
| MEAN GRASSES | 0 | 54 | 90 | 66 | 0 |

Conclusions:

11 gr/ha Select plus 0.3% v/v Adjuvant gave 80% or higher control of seven out of eight grass species. Agridex at the same rate gave 80% or higher control of four out of eight grassy species.

TABLE 6

Effect of Different Additives on the
Phytotoxicity of Select Under Field Conditions

| Herbicide rate g/ha | Additive rate % v/v | Johnson-grass | Grain Sorghum | Broadleaf Signalgrass | Grain Foxtail | Barnyard Grass |
|---|---|---|---|---|---|---|
| Select 20 | Adjuvant 0 | 1.00 | 0.67 | 0 | 0.0 | 0.0 |
| Select 20 | Adjuvant 0.5 | 5.67 | 7.67 | 6.83 | 5.00 | 7.33 |
| Select 20 | Agridex 0.5 | 1.00 | 1.33 | 0.0 | 0.0 | 0.33 |
| Select 20 | Dash 0.5 | 1.67 | 1.33 | 2.00 | 0.67 | 1.67 |
| Select 40 | Adjuvant 0 | 3.67 | 3.67 | 3.33 | 3.0 | 3.3 |
| Select 40 | Adjuvant 0.5 | 8.00 | 10.00 | 10.00 | 7.3 | 9.33 |

TABLE 6-continued

Effect of Different Additives on the
Phytotoxicity of Select Under Field Conditions

| Herbicide rate g/ha | Additive rate % v/v | Johnson-grass | Grain Sorghum | Broadleaf Signalgrass | Grain Foxtail | Barnyard Grass |
|---|---|---|---|---|---|---|
| Select 40 | Agridex 0.5 | 5.00 | 5.33 | 8.36 | 4.91 | 6.02 |
| Select 40 | Dash 0.5 | 8.17 | 7.00 | 8.00 | 6.0 | 8.17 |

Observation made 4 weeks after treatment using scale of 0–10, where 10 is complete kill of plant. 280 l/ha. spray. Fletd test: Fresno, Calif.

Dash is an adjuvant similar to those disclosed in European Patent Application 0356 812-A2.

Growth Stages at Treatment:

Johnson Grass—6–8" tall

Grain Sorghkmt—8" tall

BroadLeaf Signetgrass—1–2" tall

Green Foxtail—6–7" tall

Barnyard Grass—5–6" tall

Conclusion: The overall performance of Select +5% adjuvant was better than Select plus 0.5% of Agridex or Dash.

What is claimed is:

1. A method of enhancing uptake and transport of a plant-active agent into a living plant, said agent being capable of effecting a physiological response within said plant and said agent having a molecular structure capable of equilibrating to acidic and basic species in the presence of water; comprising the step of contacting said plant with an amount of said agent effective to obtain said physiological response in said plant in the presence of a non-phytotoxic uptake-enhancing amount of an uptake-enhancing adjuvant, said adjuvant comprising (a) 20–60% (w/w) of an anionic surfactant of the formula:

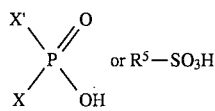

wherein X is HO— or $-(O-(CH_2)_m)_n-OR'$; X' is $-(O-(CH_2)_m)_n-OR'$;

R' is an alkyl or alkaryl group containing 5–50 carbon atoms;

m is 2 to 3; and n is an integer from 1 to about 50;

$R^5$ is linear or branched alkyl or alkenyl containing 6 to about 50 carbon atoms, or $R^5$ is

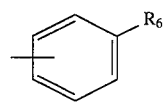

wherein $R^6$ is alkyl or alkenyl containing 1 to about 30 carbon atoms;

(b) 40–60% (w/w) of fatty acids, fatty acid esters or mixtures thereof; and (c) 10–40% (w/w) of polyalkylene glycol esters of fatty acids.

2. A method according to claim 1 wherein said plant-active agent is a herbicide, fungicide, insecticide, plant growth regulator or a mixture thereof.

3. A method according to claim 2 wherein said surfactant has a pKa in the range of 0.1 to 5.

4. A method according to claim 2 wherein said plant active agent is a herbicide.

5. A method according to claim 4 wherein said herbicide is of the formula:

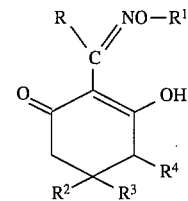

wherein

R is alkyl of 1 to 6 carbon atoms or phenyl;

$R^1$ is haloalkenyl of 2 to 6 carbon atoms and 1 to 3 halogen atoms, p-halobenzyl or p-trifluoromethylbenzyl;

$R^2$ and $R^3$ are independently hydrogen, alkyl of 1 to 3 carbon atoms, alkylthio of 1 to 6 carbon atoms, or alkylthioalkyl of 2 to 8 carbon atoms;

$R^4$ is hydrogen or carbalkoxy of 2 to 4 carbon atoms.

6. The method of claim 5 wherein $R^4$ is hydrogen.

7. The method of claim 6 wherein R is alkyl of 1 to 6 carbon atoms.

8. The method of claim 7 wherein $R^1$ is said haloalkenyl.

9. The method of claim 8 wherein one of $R^2$ and $R^3$ is hydrogen and the other is alkylthioalkyl.

10. The method of claim 9 wherein R is ethyl or propyl and one of $R^2$ or $R^3$ is hydrogen and the other is 2-ethylthiopropyl.

11. The method of claim 10 wherein $R^1$ is 3-transchloroallyl.

12. A method according to claim 1 wherein X is —OH.

13. A method according to claim 1 wherein X is $-(O-(CH_2)_m)_n-OR$.

14. A method according to claim 1 wherein said surfactant comprises a mixture of compounds wherein X=—OH and X=$-(O-(CH_2)_m)_n-OR$.

15. A method according to claim 14 wherein m=2.

16. A method according to claim 15 wherein R' is dialkylphenyl.

17. A method according to claim 16 wherein R' is dinonylphenyl.

18. A method according to claim 15 wherein n=3.

19. A method according to claim 18 wherein R' is alkyl.

20. A method according to claim 19 wherein R' is tridecyl.

21. A method according to claim 1 wherein said adjuvant comprises a combined 70% by weight of the components (b) and (c).

22. A method according to claim 1 wherein the components in (b), and (c) are selected from the group consisting of vegetable-derived oils, and mixtures thereof.

23. A method according to claim 22 wherein said components have vapor pressures less than about 3 mm of Hg at 20° C.

24. A plant-active composition comprising a plant-active agent, said agent being capable of effecting a physiological response within said plant and said agent having a molecular structure capable of equilibrating to acidic and basic Species in the presence of water comprising an amount of said agent effective to obtain said physiological response in said plant, and a non-phytotoxic uptake-enhancing amount of an uptake-enhancing adjuvant, said adjuvant comprising (a) 20–60% (w/w) of an anionic surfactant of the formula:

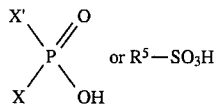

wherein X is HO— or $-(O-(CH_2)_m)_n OR'$; X' is $-(O-(CH_2)_m)_n OR'$;
R' is an alkyl or alkayl group containing 5–50 carbon atoms;
m is 2 to 3; and
n is an integer from 1 to about 50;
$R^5$ is linear or branched alkyl or alkenyl containing 6 to about 50 carbon atoms, or $R^5$ is

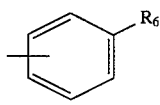

wherein $R^6$ is alkyl or alkenyl containing 1 to about 30 carbon atoms;

(b) 40–60% (w/w) of fatty acids, fatty acid esters or mixtures thereof; and (c) 10–40% (w/w) of polyalkylene glycol esters of fatty acids.

25. A composition according to claim 24 wherein said plant-active agent is a herbicide, fungicide, insecticide, plant growth regulator or a mixture thereof.

26. A composition according to claim 25 wherein said surfactant has a pKa in the range of 0.1 to 5.

27. A composition according to claim 25 wherein said plant active agent is a herbicide.

28. A composition according to claim 27 wherein said herbicide is of the formula:

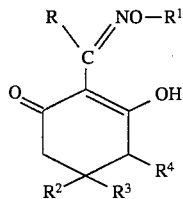

wherein
R is alkyl of 1 to 6 carbon atoms or phenyl;
$R^1$ is haloalkenyl of 2 to 6 carbon atoms and 1 to 3 halogen atom, p-halobenzyl or p-trifluoromethylbenzyl;
$R^2$ and $R^3$ are independently hydrogen, alkyl of 1 to 3 carbon atoms, alkylthio of 1 to 6 carbon atoms, or alkylthioalkyl of 2 to 8 carbon atoms;
$R^2$ is hydrogen or carbalkoxy of 2 to 4 carbon atoms.

29. The composition of claim 28 wherein $R^4$ is hydrogen.

30. The composition of claim 29 wherein R is alkyl of 1 to 6 carbon atoms.

31. The composition of claim 30 wherein $R^1$ is said haloalkenyl.

32. The composition of claim 31 wherein one of $R^2$ and $R^3$ is hydrogen and the other is alkylthioalkyl.

33. The composition of claim 32 wherein R is ethyl or propyl and one of $R^2$ or $R^3$ is hydrogen and the other is 2-ethylthiopropyl.

34. The composition of claim 33 wherein $R^1$ is 3-tran-schloroallyl.

35. A composition according to claim 24 wherein X is —OH.

36. A composition according to claim 24 wherein X is $-(O-(CH_2)_m)_n OR$.

37. A composition according to claim 24 wherein said surfactant comprises a mixture of compounds wherein X=—OH and X=$-(O-(CH_2)_m)_n OR$.

38. A composition according to claim 37 wherein m=2.

39. A composition according to claim 15 wherein R' is dialkylphenyl.

40. A composition according to claim 39 wherein R' is dinonylphenyl.

41. A composition according to claim 38 wherein n=3.

42. A composition according to claim 41 wherein R' is alkyl.

43. A composition according to claim 42 wherein R' is tridecyl.

44. A composition according to claim 24 wherein said adjuvant comprises a combined 70% by weight of the components (b) and (c) and 30% of said anionic surfactant.

45. A Composition according to claim 24 wherein the components in (b) and (c) are selected from the group consisting of vegetable-derived oils, and mixtures thereof.

46. A composition according to claim 45 wherein said components have vapor pressures less than about 3 mm of Hg at 20° C.

47. An adjuvant composition for enhancing the uptake and transport of a plant-active agent comprising (a) 20–60% (w/w) of an anionic surfactant of the formula

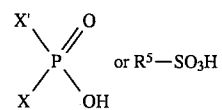

wherein X is HO— or $-(O-(CH_2)_m)_n OR'$; X' is $-(O-(CH_2)_m)_n OR'$;
R' is an alkyl or alkaryl group containing 5–50 carbon atoms;
m is 2 to 3; and n is an integer from 1 to about 50;
$R^5$ is linear or branched alkyl or alkenyl containing 6 to about 50 carbon atoms, $R^5$ is

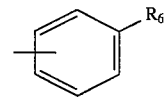

wherein $R^6$ is alkyl or alkenyl containing 1 to about 30 carbon atoms;

(b) 40–60% (w/w) of fatty acids, fatty acid esters or mixtures thereof; and (c) 10–40% (w/w) of polyalkylene glycol esters of fatty acids.

48. A composition according to claim 47 wherein X is —OH.

49. A composition according to claim 47 wherein X is $-(O-(CH_2)_m)_n OR$.

50. A composition according to claim 47 wherein said surfactant comprises a mixture of compounds wherein X=—OH and X=-(O-(CH$_2$-)$_m$-)$_n$OR.

51. A composition according to claim 50 wherein m=2.

52. A composition according to claim 51 wherein R' is dialkylphenyl.

53. A composition according to claim 52 wherein R' is dinonylphenyl.

54. A composition according to claim 51 wherein n=3.

55. A composition according to claim 54 wherein R' is alkyl.

56. A composition according to claim 55 wherein R' is tridecyl.

57. A composition according to claim 47 wherein said adjuvant comprises a combined 70% by weight of the components (b) and (c) and 30% of said anionic surfactant.

58. A composition according to claim 47 wherein the components in (b) and (c) are selected from the group consisting of vegetable-derived oils, and mixtures thereof.

* * * * *

UNITED STATES PATENT AND TRADEMARK OFFICE
CERTIFICATE OF CORRECTION

PATENT NO. : 5,554,576
DATED : September 10, 1996
INVENTOR(S) : Mookerjee et al.

It is certified that error appears in the above-indentified patent and that said Letters Patent is hereby corrected as shown below:

In column 1, line 22, after the word "the", delete -.
In column 3, line 1, after the word "bioactive", delete :.
In column 4, line 63, change "14-chloro" to read --4-chloro--.
In column 7, lines 5, 10, 15, 45, 50, move line numbers 5,10,15,45, 50 closer to col. 8.
In column 9, line 45, -- remove line number 45--.
In column 11, line 15, change "Fletd" to read -- Field--.
In column 11, line 21, change "Sorghkmt" to read --Sorghum--.
In column 11, line 22, change "Signetgrass" to read --Signalgrass--.
In column 11, line 25, change "+5%" to read --+0.5%--.
In column 13, line 7, change "Species" to read --species--.
In column 13, line 21, change "alkayl" to read --alkaryl--.
In column 13, line 59, change "atom" to read --atoms--.
In column 13, line 64, change " $R^2$ " to read -- $R^4$ --.

Signed and Sealed this

Twenty-eighth Day of October, 1997

*Attest:*

BRUCE LEHMAN

*Attesting Officer*      *Commissioner of Patents and Trademarks*